(12) United States Patent
Bedos et al.

(10) Patent No.: US 9,084,730 B2
(45) Date of Patent: Jul. 21, 2015

(54) PHARMACEUTICAL COMPOSITION COMPRISING A SOLID DISPERSION WITH A POLYMER MATRIX CONTAINING A CONTINUOUS POLYDEXTROSE PHASE AND A CONTINUOUS PHASE OF A POLYMER OTHER THAN POLYDEXTROSE

(75) Inventors: Michel Bedos, Viols-Le-Fort (FR); Thierry Breul, Frontignan (FR); Stephen Byard, Morpeth (GB); Isabel Ribeiro Dos Santos, Toulouse (FR)

(73) Assignee: SANOFI, Paris (FR)

( * ) Notice: Subject to any disclaimer, the term of this patent is extended or adjusted under 35 U.S.C. 154(b) by 1586 days.

(21) Appl. No.: 11/686,611

(22) Filed: Mar. 15, 2007

(65) Prior Publication Data
US 2007/0243257 A1 Oct. 18, 2007

Related U.S. Application Data

(63) Continuation of application No. PCT/FR2005/002288, filed on Sep. 15, 2005.

(30) Foreign Application Priority Data

Sep. 17, 2004 (FR) .................................... 04 09874

(51) Int. Cl.
*A61K 9/20* (2006.01)

(52) U.S. Cl.
CPC ............... *A61K 9/205* (2013.01); *A61K 9/2027* (2013.01); *A61K 9/2095* (2013.01)

(58) Field of Classification Search
CPC .... A61K 9/2027; A61K 9/205; A61K 9/2095
See application file for complete search history.

(56) References Cited

U.S. PATENT DOCUMENTS

| | | | |
|---|---|---|---|
| 4,828,836 A | | 5/1989 | Elger et al. |
| 5,501,858 A | * | 3/1996 | Fuisz .............................. 424/439 |
| 5,624,941 A | * | 4/1997 | Barth et al. .................... 514/326 |
| 5,935,600 A | | 8/1999 | Cherukuri et al. |
| 6,462,093 B1 | * | 10/2002 | Miyamoto et al. ......... 514/772.3 |
| 6,933,335 B1 | | 8/2005 | Berger et al. |
| 2003/0003145 A1 | * | 1/2003 | Abramovici et al. ......... 424/465 |
| 2003/0083309 A1 | | 5/2003 | Adeyeye et al. |

FOREIGN PATENT DOCUMENTS

| | | | |
|---|---|---|---|
| EP | 0240904 | * | 3/1987 |
| EP | 0240904 A2 | * | 3/1987 |
| EP | 0679339 | | 11/1995 |
| JP | 62-292732 | | 12/1987 |
| WO | WO 03/000294 A1 | | 1/2003 |

OTHER PUBLICATIONS

EP 0240904 translation, publcation date: Mar. 1987, translated Jul. 20, 2010, pp. 1-4.*
Rasmussen, Seren, Acta Pharmacol. et. toxicol. 1966, 24, 331-345.*
Craig, S.A.S. et al., Cereal Food World, May 1998, vol. 43, No. 5, pp. 370-376.*
Machine translation of EP0240904, translated Jul. 20, 2010.*
Craig, S.A.S.; Holden, J.f.; Troup, J.P.; AUerbach, M.H.; Frier, H.I. "Polydextrose as soluble fiber: Physiological and Analytical Aspects" Cereal Food World, May 1998, 43 (5), 370-376.*
Official Action dated Sep. 6, 2011 received from the Japanese Patent Office from related Japanese Application No. 2007-531798, together with an English-language translation.

* cited by examiner

*Primary Examiner* — Sean Basquill
*Assistant Examiner* — Andrew S Rosenthal
(74) *Attorney, Agent, or Firm* — Morrison & Foerster LLP

(57) ABSTRACT

The present invention relates to a solid pharmaceutical composition comprising a solid dispersion containing at least one active principle and a pharmaceutically acceptable polymer matrix,
 a characterized in that said pharmaceutically acceptable polymer matrix comprises a blend of (i) polydextrose, in the form of a continuous polydextrose phase, in order to promote the disintegration of the composition in an aqueous medium, and (ii) at least one polymer other than polydextrose, in the form of a continuous phase of this polymer, whereby the polydextrose is in a concentration of at least 20 wt % and the at least one polymer other than polydextrose is in a concentration of at least 20 wt % in relation to the total weight of said pharmaceutically acceptable polymer matrix.

26 Claims, 3 Drawing Sheets

PHARMACEUTICAL COMPOSITION COMPRISING A SOLID DISPERSION WITH A POLYMER MATRIX CONTAINING A CONTINUOUS POLYDEXTROSE PHASE AND A CONTINUOUS PHASE OF A POLYMER OTHER THAN POLYDEXTROSE

CROSS REFERENCE TO RELATED APPLICATIONS

This application is a continuation of International application No. PCT/FR2005/002,288, filed Sep. 15, 2005, which is incorporated herein by reference in its entirety; which claims the benefit of priority of French Patent Application No. 04/09,874, filed Sep. 17, 2004.

BACKGROUND OF THE INVENTION

1. Field of the Invention

The present invention relates to a novel pharmaceutical composition comprising a solid dispersion of at least one active principle in a pharmaceutically acceptable polymer matrix comprising at least one continuous polydextrose phase and at least one continuous phase of a polymer other than polydextrose.

2. Description of the Art

Pharmaceutical compositions in the form of solid dispersions of active principles are well known to those skilled in the art. They are generally used to improve the solubility of active principles, to control their rate of release or to improve their bioavailability.

Many active principle molecules have a low bioavailability when taken orally. A low solubility in an aqueous medium (i.e. a solubility in water at 25° C. of less than 1 mg/ml), but also a poor permeability, may be responsible for their weak absorption after oral administration. Numerous techniques have been used in order to improve the bioavailability of these molecules when administered orally. This is the case of micronization, the formation of salts and complexes, solubilization in liquids and solid dispersions.

The concept of solid dispersions was introduced in 1961 by Sekiguchi and Obi (Chem. Pharm. Bull. 9, (1961), 866-872), and then taken up and defined by Goldberg in 1965 (J. Pharm. Sci. 54, (1965), 1145-1148) and Chiou and Riegelmann in 1971 (J. Pharm. Sci. 60(9), (1971) 1281-1302).

In general, the expression "solid dispersion" denotes a matrix in the solid state, as opposed to the liquid or gas state, comprising at least two constituents, the first of which, for example a pharmaceutical active principle, is dispersed as uniformly as possible within the other constituents, for example a pharmaceutically acceptable matrix. When the distribution consists of a single phase, such a "solid dispersion" will more particularly be called a "solid solution": the dispersion takes place on a molecular scale, the active principle is then solubilized in the solid matrix and is in the amorphous state. When the solid solution is brought into contact with a liquid medium, such as the gastric medium, it can then readily form a liquid solution. When the distribution does not consist of a single phase, the expression "solid dispersion" is used: the dispersion takes place on a particulate scale (=50 nm). The active principle is either completely dispersed therein in the crystalline state, or partially solubilized therein.

There exists mainly two methods of preparing a "solid dispersion":

the "solvent" approach, based on the solubilization of the components (active principle and matrix) in a common solvent, followed by evaporation of the solvent;

the "molten" approach which consists in melting the components (active principle and matrix) at high temperature and then in cooling the mixture in order to allow solidification.

The "solvent" approach has many drawbacks: implementation is complex, there is in particular a multitude of steps related to the treatment of the solvents, resulting in a high cost, and also environmental and public health problems (residual contents of solvents).

The "molten" approach does not have such drawbacks, but requires the use of high temperatures that can affect the chemical stability of the active principles and of the other components of the solid dispersion.

The solid dispersions included in the pharmaceutical compositions of the prior art are, in general, formed from an active principle dissolved or dispersed in a matrix of one or more pharmaceutically acceptable polymer(s).

Patent applications EP 0 240 904 and EP 0 240 906 (BASF AG) thus describe a process for preparing solid pharmaceutical forms by means of an extrusion or injection-molding process, preferably using N-vinylpyrrolidone copolymers, in particular copovidone.

Nevertheless, the compositions of the prior art comprising solid dispersions do not always make it possible to obtain, in particular, a satisfactory increase in the bioavailability of relatively water-insoluble active principles, due to the very fact of this low solubility all along the gastrointestinal tract.

All of the references described herein are incorporated herein by reference in their entirety.

SUMMARY OF THE INVENTION

It has now been found, entirely surprisingly and unexpectedly, that a novel pharmaceutical composition comprising a solid dispersion having a particular polymer matrix makes it possible to advantageously increase the bioavailability of an active principle compared with the already known soluble dispersions.

The subject of the present invention is thus a solid pharmaceutical composition comprising a solid dispersion containing at least one active principle and a pharmaceutically acceptable polymer matrix, characterized in that said pharmaceutically acceptable polymer matrix comprises a blend of (i) polydextrose, in the form of a continuous polydextrose phase, and (ii) at least one polymer other than polydextrose, in the form of a continuous phase of this polymer, the proportion of said polydextrose being at least 20% by weight and the proportion of said at least one polymer other than polydextrose being at least 20% by weight, relative to the total weight of said pharmaceutically acceptable polymer matrix.

In particular, the pharmaceutical composition according to the invention is characterized in that it can be obtained by means of a process comprising at least one step consisting in producing a compound containing said at least one active principle, said polydextrose and said at least one polymer other than polydextrose, in a screw mixer and at a mixing temperature of between approximately 50° C. and approximately 250° C.

DETAILED DESCRIPTION OF THE INVENTION

Figure 1:
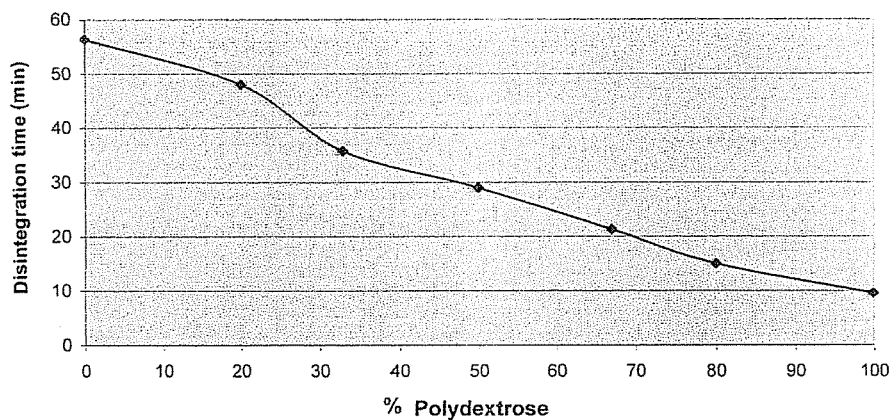
FIG. 1 is a curve showing the disintegration time (in minutes) of molded tablets (preparations 1 to 7 of example 4), as a function of the percentage of polydextrose in a polydextrose and copovidone polymer matrix, expressed relative to the total weight of this polymer matrix, according to the in vitro disintegration test (section 4.1 of example 4; table 4).

More particularly, a subject of the present invention is a solid pharmaceutical composition comprising a solid dispersion containing at least one active principle and a pharmaceutically acceptable polymer matrix, characterized in that said pharmaceutically acceptable polymer matrix comprises a blend of (i) polydextrose, in the form of a continuous polydextrose phase, in order to promote the disintegration of the composition in an aqueous medium, and (ii) at least one polymer other than polydextrose, in the form of a continuous phase of this polymer, the proportion of said polydextrose being at least 20% by weight and the proportion of said at least one polymer other than polydextrose being at least 20% by weight, relative to the total weight of said pharmaceutically acceptable polymer matrix, and in that this pharmaceutical composition can be obtained by means of a process comprising at least one step consisting in producing a compound containing said at least one active principle, said polydextrose and said at least one polymer other than polydextrose, in a screw mixer and at a mixing temperature of between approximately 50° C. and approximately 250° C.

The pharmaceutical composition according to the invention is most particularly suitable for oral administration.

According to the invention, the term "solid dispersion" is intended to mean a dispersion of at least one active principle in a pharmaceutically acceptable polymer matrix, in the form of a solid solution (active principle dispersed in the amorphous state, solubilized in the polymer matrix) or not (active principle dispersed in the crystalline state) or in an intermediate form (active principle partly dispersed in the amorphous state and partly in the crystalline state).

According to the invention, the term "continuous phase" of a given polymer (polydextrose or other) is intended to mean that said polymer constitutes a fraction of the polymer matrix and is not in the dispersed state, i.e. is spread without discontinuity throughout the three dimensions of the solid dispersion.

The pharmaceutically acceptable polymer matrix of the composition according to the invention thus comprises a blend of at least two continuous polymer phases, i.e. a blend of said polydextrose, in the form of a first continuous phase, and of said at least one polymer other than polydextrose, in the form of at least one other continuous phase, these distinct continuous polymer phases not being discretely dispersed in one another.

It has been noted that this characteristic structure of the composition according to the invention results, firstly, from the respective polymer content (at least 20% by weight, relative to the total weight of said pharmaceutically acceptable polymer matrix) and, secondly, from the step consisting of the process for producing a compound of the components for said solid dispersion using a screw mixer and at a mixing temperature of between 50° C. and approximately 250° C. (shear and plasticizing effect on a compound at this temperature using a screw mixer such as that of an extrusion or injection-molding device), without, however, wishing to be bound by any theory.

According to the present invention, it is to be noted that the polydextrose, in the form of a continuous polydextrose phase of a polymer matrix also comprising a polymer other than polydextrose, also in the form of a continuous phase, in a pharmaceutical composition comprising a solid dispersion of an active principle in such a polymer matrix, which is in particular bicontinuous, as the function of promoting the disintegration of the pharmaceutical composition in an aqueous medium.

According to the present invention the expression "promoting the disintegration of the pharmaceutical composition" is intended to mean the acceleration of the disintegration of the solid dispersion in an aqueous medium. The disintegration capacity is determined according to the disintegration assay described in section 2.9.1 of the European Pharmacopeia.

Without, however, wishing to be bound by any theory, the improved disintegration in the stomach, as provided by the presence of the continuous polydextrose phase in the pharmaceutical composition according to the invention, should make it possible to advantageously reduce the risks of local concentrations and therefore of precipitation of said active principle in particular in the gastrointestinal tract.

Polydextrose (CAS No. 068424044) is a water-soluble amorphous polymer comprising glucose units linked randomly via glucoside bonds of all types (predominantly 1, 6) and also minor contents in particular of glucose and sorbitol units. A polydextrose preparation has been described in particular in patents U.S. Pat. Nos. 3,766,165 and 3,876,794 from the company Pfizer Inc., both of which are incorporated herein by reference in their entirety. Polydextrose can, in general, be obtained by means of a process comprising a step consisting of a catalytic condensation reaction using a mixture comprising D-glucose, of sorbitol and an acid catalyst, in particular citric acid or phosphoric acid.

The use of polydextrose was first developed in the food industry, in particular dietetics, given its partial metabolism and therefore its low calorie content. Polydextrose is, for example, mentioned in the "Food Chemicals Codex" (FCC, 4th edition, 1996).

Polydextrose can advantageously be purified, in particular by conventional ion exchange resin separation techniques, in order to remove residual products therefrom so as to further improve its organoleptic (acidity) and/or color properties (see, for example, EP 0 458 748 or EP 0 473 333), in the context of use in food products, but also from now on, with a view to its use in the pharmaceutical field, for example, as an excipient (Pharmaceutical Excipients 2001, edited by Ray C Rowe, Paul J Sheskey and Paul J Weller, polydextrose monography, Jul. 27, 2001).

According to the present invention, the term "polydextrose" is thus intended to mean, of course, a pharmaceutically acceptable polydextrose. In particular, a pharmaceutically acceptable polydextrose preferably has a purity of at least 90% by weight of polydextrose, the remaining components predominantly comprising free glucose, sorbitol, and levoglucosan (1,6-anhydro-D-glucose) units and water, it being possible for the purity to be determined by UV spectrophotometry on a dried substance.

The polydextrose that can be used in the composition according to the invention preferably has a molecular weight of at most 22 000 g/mol, as measured in a known manner by gel permeation chromatography (or "exclusion chromatography") with a refractometric detector.

In particular, the polydextrose that can be used in the composition according to the invention has an average molecular weight of between 150 and 5000, in particular between 1000 and 2000.

Among polydextroses that can be used in the composition according to the invention, mention may, in particular, be made of the polydextroses sold by the company Pfizer under the names "polydextrose A" and "polydextrose K", which have an average molecular weight of between 1200 and 2000, and the family of polydextroses sold by the company Danisco under the name "Litesse®", such as "Litessee® II", and more particularly "Litesse® Ultra™" having an average molecular weight of between 182 and 5000.

Of course, according to the invention, the term "polydextrose" can include a single given polydextrose or a blend of polydextroses, in particular, among those mentioned above, for constituting said continuous polydextrose phase.

The polymer "other than polydextrose" included in the polymer matrix of the composition according to the invention may be any polymer that can be used in the solid dispersions of the prior art, and of course a polymer other than polydextrose as defined above.

Of course, the polymer other than polydextrose can comprise a blend of several polymers other than polydextrose, which are distinct from but miscible with one another.

In particular, said at least one polymer other than polydextrose is selected from the group comprising:
cellulose-based polymers, such as alkylcelluloses, in particular methylcellulose, such as hydroxyalkylcelluloses, in particular hydroxymethylcellulose, hydroxyethylcellulose, hydroxypropylcellulose, hydroxybutylcellulose and weakly substituted hydroxypropylcellulose, such as hydroxyalkylalkylcelluloses, in particular hydroxyethylmethylcellulose and hydroxypropylmethylcellulose, such as carboxyalkylcelluloses, in particular carboxymethylcellulose, such as carboxyalkylcellulose salts, in particular sodium carboxymethylcellulose, such as carboxyalkylalkylcelluloses, in particular carboxymethylethylcellulose, and such as esters of cellulose derivatives, in particular hydroxypropylmethylcellulose phthalate, hydroxypropylmethylcellulose acetate succinate and cellulose acetate phthalate;
vinyl homo- and copolymers, such as N-vinylpyrrolidone polymers, in particular povidone, copovidone and polyvinyl alcohol;
acrylic and methacrylic polymers, such as those sold under the name Eudragit® by the company Röhm, in particular Eudragit® E 100 and Eudragit® L 100-55;
chemically modified starches, in particular starches derived from starches extracted in particular from maize, from potato, from rice, from wheat or from tapioca;
pectins;
chitin derivatives such as chitosan;
polymers of natural origin, such as gum tragacanth, gelatin, sodium alginate, pullulan, gum arabic, guar gum, agar-agar and xanthan gum;
polyalkylene oxides, such as polyethylene oxides, polypropylene oxides and copolymers of ethylene oxide and of propylene oxide;
and blends thereof.

More particularly, said at least one polymer other than polydextrose is selected from the group comprising methylcellulose, hydroxymethylcellulose, hydroxyethylcellulose, hydroxypropylcellulose, hydroxybutylcellulose, weakly substituted hydroxypropylcellulose, hydroxyethylmethylcellulose, hydroxypropylmethylcellulose, carboxymethylcellulose, sodium carboxymethylcellulose, carboxymethylethylcellulose, hydroxypropylmethylcellulose phthalate, hydroxypropylmethylcellulose acetate succinate, cellulose acetate phthalate, povidone, copovidone, polyvinyl alcohol, acrylic and methacrylic polymers, such as those sold under the name Eudragit® by the company Röhm, in particular Eudragit® E 100 and Eudragite® L 100-55, starches derived from starches extracted from maize, from potato, from rice, from wheat or from tapioca, pectins, chitosan, gum tragacanth, gelatin, sodium alginate, pullulan, gum arabic, guar gum, agar-agar, xanthan gum, polyethylene oxides, polypropylene oxides, copolymers of ethylene oxide and of propylene oxide, and blends thereof.

The polymer other than polydextrose can be used in the composition according to the invention is in particular selected from the group comprising hydrophilic polymers other than polydextrose, and blends thereof, and is more particularly selected from the group comprising:
hydroxypropylcellulose, such as that sold under the name Klucel® by the company Aqualon;
hydroxyethylcellulose, such as that sold under the name Natrosol® by the company Aqualon;
cationic copolymers of dimethylaminoethyl methacrylates and of neutral methacrylic esters, such as those sold under the name Eudragit® E 100 by the company Röhm;
anionic copolymers of methacrylic acid and of methacrylic acid esters, such as those sold under the name Eudragit® L 100-55 by the company Röhm;
hydroxypropylmethylcellulose acetate succinate, such as that sold under the name Aqoat® by the company Shin-Etsu;
polyethylene glycols, preferably those having a molecular weight greater than 1500;
copovidone, i.e. the copolymer (poly(N-vinylpyrrolidone) 60% —vinyl acetate 40%) as sold under the name Kollidon VA 64® by the company BASF,
and blends thereof.

It has been possible to note in particular that said at least one polymer other than polydextrose, as defined above, more particularly when said at least one polymer other than polydextrose is a hydrophilic polymer other than polydextrose, as defined above, can solubilize part of the polydextrose included in said pharmaceutically acceptable polymer matrix: said continuous phase of said at least one polymer other than polydextrose can thus be in the form of a solid solution of polydextrose in said at least one polymer other than polydextrose, this continuous phase being distinct from said continuous polydextrose phase. Thus, in particular, the composition according to the invention is characterized in that said at least one polymer other than polydextrose, in particular when said at least one polymer other than polydextrose is a hydrophilic polymer other than polydextrose as defined above, is in the form of a continuous phase of a solid solution of polydextrose in said at least one polymer other than polydextrose, this continuous phase being distinct from said continuous polydextrose phase.

According to a specific embodiment of the present invention, the polymer matrix of the composition according to the invention comprises only two continuous polymer phases, i.e. a first continuous polydextrose phase and a second continuous phase of said at least one polymer other than polydextrose, the pharmaceutical composition according to the invention thus characteristically exhibiting a polymer matrix with a bicontinuous structure essentially consisting of a continuous polydextrose phase and of a continuous phase of said at least one polymer other than polydextrose.

The expression "bicontinuous structure" is known to describe, in general, a structure where considerable fractions of molecules of two different compounds (or different phases) form domains which extend without discontinuity in the three spatial dimensions (according to Lindman et al., 1989). The bicontinuous structures are thus characterized by a separation surface, known as interface, that crosses the entire sample, dividing it in to two distinct and contiguous, interwoven labyrinths. Thus, the two sub-volumes (or sub-spaces), of each part of this interface, which are occupied by each of the compounds (or phases) are continuous (according to Schwarz and Gomper, 2002). The two labyrinths can then be used, independently of one another, to cross the sample from part to part: it is thus possible for each compound (or phase) to connect any two points located within said compound (or said phase), via a path that passes only through this same compound (or this same phase).

The obtaining of bicontinuous polymeric solid structures by extrusion is described in the literature, in fields other than the pharmaceutical field, in particular in patent application WO 01 109 49, and in the pharmaceutical domain, in particular in the article by Dollinger and Sawan, Polymer Preprints, 1990, 31: 211-212, which describes the use of a PLA/PE-PVAc blend in which the function of the PE-PVAc phase is to reinforce/consolidate the matrix.

The demonstration of bicontinuous structures in a liquid medium using NMR self-diffusion coefficient measurements has been extensively described in the literature, for instance in the article "Demonstration of bicontinuous structures in microemulsions using automatic-mode NMR self-diffusion measurements" by K. P. Datema et al., published in Magnetic Resonance in Chemistry Vol. 30, 760-767 (1992), or in the article "On the demonstration of bicontinuous structures in microemulsions" by B. Lindman et al., published in Colloids and Surfaces, 38 (1989) pages 205 to 224. In the case of solid media formed from polymer blends, several studies concerning the theoretical predictivity of the obtaining of bicontinuous structures have been published ("Interfacial and topological measurements of bicontinuous polymer morphologies" by H. Jinnai et al., in Physical Review Vol. 64 010803 (2001) or "Structuring polymer blends with bicontinuous phase morphology" by J Lyngaae-Jorgensen et al., in Polymer 44 (2003) 1661-1669); as have results of microscopic observations or of porosymmetry of structures of polymer blends which do not invalidate these predictions ("Bicontinuous morphologies in homologous multiblock copolymers and their homopolymer blends" by J. H. Laurer et al., in Macromolecules 1998, 31, 7546-7549 or "Observation of fine structure in bicontinuous phase-separated domains of a polymer blend by laser scanning confocal microscopy" by H. Jinnai et al., in Macromolecules 2001, 34 5186-5191 or "Bicontinuous nanoporous polymers by carbon dioxide foaming" by B. Krause et al., in Macromolecules 2001, 34, 8792-8801).

In order to demonstrate the continuity of a solid phase in a multiphase solid mixture, it is possible to use solid nuclear magnetic resonance (NMR) analysis techniques, in particular measurements of proton nuclear relaxation times. In this type of NMR analysis, the atomic nuclei are excited at an energy state above that of the equilibrium state. The excited nuclei lose energy through the interactions between the spins of adjacent nuclei (spin-spin interactions) and through the interactions with the surrounding medium (spin-lattice interactions). Measuring these processes of relaxation of the proton nuclei of a molecule makes it possible to experimentally observe the molecular mobility of this molecule in its environment. The two parameters that can be measured experimentally by this technique are:

"T1", corresponding to the proton relaxation time in a fixed frame of reference, the measurement of which is of the order of magnitude of a second, and which characterizes domains (or phases) of the order of 50 nm, and "T1ρ" or "T1 Rho", corresponding to the proton relaxation time in a rotating frame of reference, the measurement of which is of the order of magnitude of a millisecond, and which characterizes domains (or phases) of between 5 nm and 50 nm.

In the case of a solid polymer blend, if a single value for T1 is obtained, this indicates that the polymer blend is homogeneous and that it is not possible to separate a discrete domain of greater than 50 nm in size from one phase dispersed in another: the blend is then a solid solution on a 50 nm scale.

Similarly, if a single value for T1 Rho is obtained, this indicates that the polymer blend is homogeneous and that it is not possible to separate a discrete domain of greater than 5 nm in size from one phase dispersed in another: the blend is then a solid solution on a 5 nm scale.

On the other hand, if in the case of a solid blend of two polymers, two values are obtained for T1 Rho, this means that the blend is made up of two distinct phases (or domains). In the latter case, if the T1 Rho value attributed to a polymer does not vary according to its concentration in the blend, it may be concluded from this that this polymer forms a continuous phase consisting of the polymer alone. If, on the other hand, the T1 Rho value attributed to a polymer varies according to its concentration in the blend, it may be concluded from this that this polymer is part of the composition of a phase consisting of the two polymers dispersed in one another on a scale of between 5 nm and 50 nm, a size which is of the order of magnitude of one polymer molecule, and, in this case, the blend is a solid solution of one polymer in the other.

Thus, according to a specific embodiment, the pharmaceutical composition according to the invention is characterized in that said pharmaceutically acceptable polymer matrix has a bicontinuous structure essentially consisting of a continuous phase of said polydextrose and of a continuous phase of said at least one polymer other than polydextrose.

More particularly, the pharmaceutical composition according to the invention is characterized in that said pharmaceutically acceptable polymer matrix has a bicontinuous structure essentially consisting of a continuous phase of said polydextrose and of a continuous phase of said at least one polymer other than polydextrose selected from the group comprising hydrophilic polymers and blends thereof, as described above, i.e. more particularly the group comprising hydroxypropylcellulose, hydroxyethylcellulose, cationic copolymers of dimethylaminoethyl methacrylates and of neutral methacrylic esters, anionic copolymers of methacrylic acid and of methacrylic acid esters, hydroxypropylmethylcellulose acetate succinate, polyethylene glycols, copovidone, and blends thereof.

As indicated above, it has been noted that the characteristic structure of the composition according to the invention results in particular from the respective contents of polymers (at least 20% by weight, relative to the total weight of said pharmaceutically acceptable polymer matrix).

In particular, the pharmaceutical composition according to the invention is characterized in that the proportion of said polydextrose is between approximately 20% and approximately 80% by weight, and in that the proportion of said at least one polymer other than polydextrose is between approximately 20% and approximately 80% by weight, relative to the total weight of the pharmaceutically acceptable polymer matrix.

According to a specific embodiment, the weight ratio of said polydextrose to said at least one polymer other than polydextrose, in the polymer matrix of the pharmaceutical composition according to the invention, is between approximately 20:80 and approximately 50:50.

The proportion of said pharmaceutically acceptable polymer matrix, in the pharmaceutical composition according to the invention, may in particular be between approximately 50% and approximately 99.9% by weight, relative to the total weight of the composition.

According to the invention, the term "active principle", is intended to mean a medicinal substance intended, after administration, to bring about a preventive of therapeutic response, and also a combination of two or more substances of this type.

The composition according to the invention can contain any active principle know to those skilled in the art, irrespective of the therapeutic application envisioned.

Of course, the active principle should, however, be suitable for the conditions of said step consisting in producing a compound in a screw mixer and at a mixing temperature of between approximately 50° C. and approximately 250° C., as described hereinafter.

The active principle may be in the form of a solvated or nonsolvated pharmaceutically acceptable salt, or in the form of a complex, in particular with cyclodextrins, in particular hydroxypropyl-beta-cyclodextrin.

The composition according to the invention is more particularly suitable for the administration of an active principle that is difficult to dissolve in water. Thus, in particular, said at least one active principle may have a moderate solubility in an aqueous medium, i.e. a water-solubility of less than 10 mg/ml at 25° C., a low solubility in an aqueous medium, i.e. a water-solubility of less than 1 mg/ml at 25° C., or even a very low solubility in an aqueous medium, i.e. a water-solubility of less than 0.1 mg/ml at 25° C.

In the composition according to the invention, said at least one active principle is dispersed in said pharmaceutically acceptable polymer matrix, either in the amorphous state, or in the crystalline state, preferably predominantly in the amorphous state, the presence of the active principle in the amorphous state promoting in particular its solubilization in a liquid solution.

According to the invention, the term "predominantly in the amorphous state" is intended to mean that more than 50% of the total mass of said at least one active principle dispersed in said pharmaceutically acceptable matrix is in the amorphous state.

The amorphous or crystalline arrangement of the active principle can be verified by differential enthalpy analysis or by X-ray diffraction study, but also by microscopy techniques.

As active principle that can be used in the composition according to the invention, mention may in particular be made of:

N-piperidino-5-(4-bromophenyl)-1-(2,4-dichlorophenyl)-4-methylpyrazole-3-carboxamide;

N-piperidino-5-(4-chlorophenyl)-1-(2,4-dichlorophenyl)-4-methylpyrazole-3-carboxamide;

amiodarone (or 2-n-butyl-3-[3,5-diiodo-4-diethylaminoethoxy-benzoyl]benzofuran) or pharmaceutically acceptable salts thereof, in particular the hydrochlorides;

dronedarone (or 2-n-butyl-3-[4-(3-di-n-butylaminopropoxy) benzoyl]-5-methylsulfonamidobenzofuran) and pharmaceutically acceptable salts thereof, in particular the hydrochlorides;

2-[1-(7-chloroquinolin-4-yl)-5-(2,6-dimethoxyphenyl)-1H-pyrazole-3-carbonyl]amino-adamantane-2-carboxylic acid;

isopropyl 2-n-butyl-3-[4-[3-(dibutylamino)propyl]benzoyl]-1-benzofuran-5-carboxylate and pharmaceutically acceptable salts thereof, in particular the fumarate;

7-chloro-N,N,5-trimethyl-4-oxo-3-phenyl-3,5-dihydro-4H-pyridazino[4,5-b]indol-1-acetamide.

and combinations of these active principles.

The proportion of said active principle depends in particular on the intrinsic solubility of the active principle, on the effective dose required and on the desired dissolution profile.

The proportion of said active principle in the composition according to the invention can in particular be between approximately 0.1% and approximately 50% by weight, relative to the total weight of the composition. The equivalent doses of active principles are of the order of one milligram to one gram, per unit dose.

The pharmaceutical composition according to the invention can also comprise any component known to those skilled in the art for a pharmaceutical composition, in particular those for a pharmaceutical composition comprising a solid dispersion. In particular, the pharmaceutical composition according to the invention is characterized in that said compound produced in a screw mixer can also contain at least one component selected from the group comprising plasticizers, demolding agents or lubricants, fluidifying agents, antioxidants, preserving agents, dyes, flavorings, sweeteners, wetting agents, buffers, adsorbents, absorption promoters, in particular vitamin E (d-α-tocopheryl polyethylene glycol 1000 succinate) such as that sold under the name Eastman® Vitamin E TPGS by the company Eastman, bioadhesive agents, disintegrating agents and mixtures thereof.

As indicated above, it has been noted that the characteristic structure of the composition according to the invention results not only from the respective contents of polymers (at least 20% by weight, relative to the total weight of said pharmaceutically acceptable polymer matrix) but also from the step consisting of the process consisting in producing a compound of the components for said solid dispersion using a screw mixer and at a mixing temperature of between approximately 50° C. and approximately 250° C. (shear and plasticizing effect on a compound at this temperature, using a screw mixer such as that of an extrusion or injection-molding device).

More particularly, said mixing temperature is between approximately 80° C. and approximately 200° C., and even more particularly between approximately 100° C. and approximately 160° C.

The mixing temperature is in particular regulated so as to be above the glass transition temperature of the compound, it being possible for this mixing to be carried out for a period of time sufficient to obtain plasticization of the compound, solubilization of the active principle, and thus, in particular, formation of said continuous phases of polydextrose and of said polymer other than polydextrose, essentially free of heterogeneities. The formation of these continuous phases can, for example, be verified by solid-state NMR measurements of proton relaxation time, as described above and illustrated in the examples hereinafter.

This mixing temperature is preferably regulated at a temperature that is suitable for the active principle. It can, for example, be decreased so as to prevent too great a disintegration of the active principle, for a given polymer matrix, according to techniques known to those skilled in the art, in particular by introduction of at least one plasticizer, in order to reduce the glass transition temperature of the polymer matrix, such as triethyl citrate, ethylene glycol, triethylene glycol, polyethylene glycol, polypropylene glycol, copolymers of ethylene glycol and of propylene glycol, a poloxamer or water.

The mixing temperature can be obtained in particular by virtue of heating means integrated into the screw mixer.

The components of the compound intended to be produced in said screw mixer, i.e. at least said at least one active principle, said polydextrose and said at least one polymer other than polydextrose, can be introduced into the screw mixer individually and/or as a mixture of at least some of them.

For example, the components can be introduced in the form of a simple homogenous preliminary mixture or "physical mixture", produced at ambient temperature (approximately 25° C.) in a conventional mixer, for example of the Turbula type.

According to another example, the polymer other than polydextrose can be introduced into said screw mixer in the form of a mixture with at least part of the total amount of polydextrose of the composition according to the invention, at least part of the total amount of said at least one active principle and at least part of the total amount of possible additive(s), it being possible for this mixture to be in particular in the form of a simple physical mixture or in the form of a solid dispersion or else in the form of a solid solution, the rest of the components of the present composition, i.e. at least the rest of the polydextrose, the rest of said at least one active principle and the rest of the possible additive(s), being introduced with this mixture into the screw mixer so as to obtain the composition according to the invention. Conversely, of course, the polydextrose can be introduced into said screw mixer in the form of a mixture with at least part of the total amount of said polymer other than polydextrose, at least part of the total amount of said at least one active principle and at least part of the total amount of possible additive(s), it being possible for this mixture to be in particular in the form of a simple physical mixture or in the form of a solid dispersion or in the form of a solid solution, the rest of the components of the present composition, i.e. at least the rest of said polymer other than polydextrose, the rest of said at least one active principle and the rest of the possible additive(s), being introduced with this mixture into the screw mixer so as to obtain the composition according to the invention.

The screw mixer can thus be in particular selected from the known devices for extrusion (single-screw or multiscrew extruder) or injection molding of plastics. Various screw geometries may be suitable, in particular according to the composition of the compound.

According to a specific embodiment of the present invention, said screw mixer is a twin-screw mixer, one of the advantages of which is in particular that it provides a greater shear force on the compound. The twin-screw mixer can operate by corotation or counterrotation.

According to a particularly preferred embodiment of the present invention, said screw mixer is an extrusion device, such as, for example, the device sold under the name Poly-Drive Extruder® by the company Thermo Haake. More particularly, said step consisting in producing said compound in an extrusion device can be advantageously followed by at least one step consisting in forming the extruded compound, at the temperature of the extruded compound or after cooling of the extruded compound to a suitable forming temperature, selected from the group comprising calendering, spinning and cutting steps, and combinations of these steps.

According to another particularly preferred embodiment of the present invention, said screw mixer is an injection-molding device, such as, for example, the injection-molding machine sold under the name "Sprinter 11" by the company Erinca.

If necessary, the mixing step in the screw mixer can be preceded by a step consisting of physical mixing at a suitable temperature, in particular between ambient temperature (approximately 25° C.) and the temperature of the compound in the screw mixer, for example in a Turbula® mixer, for a period of time sufficient (in general of a few minutes) to obtain a homogeneous physical mixture, in particular with a view to facilitating the feeding of said screw mixer.

Irrespective of the screw mixer used, the pharmaceutical composition according to the invention is more particularly characterized in that said process also comprises, after cooling to a suitable temperature for sufficiently solidifying the compound obtained, at least one step selected from the group comprising milling and cuffing steps, and combinations of these steps.

Of course, the composition can comprise a coating, such as those known to those skilled in the art, in particular, for improving the appearance and/or the taste and/or providing an effect of modified release of the active principle.

In particular, the disintegration of the pharmaceutical composition promoted in particular by the polydextrose in the form of a continuous phase, as explained above, does not, of course, exclude an immediate release or a modified (slow or delayed) release, or a combination of these types of release, from the fragments of the disintegrated composition, using formulation techniques known to those skilled in the art, in particular a coating for a modified release.

Thus, the pharmaceutical composition according to any one of the preceding claims may be more particularly characterized in that it can be obtained by means of a process also comprising at least one coating step for modified release.

The present invention also relates to a solid pharmaceutical form, characterized in that it comprises at least one pharmaceutical composition as described above, in particular to a solid pharmaceutical form for oral administration.

More particularly, a subject of the present invention is a pharmaceutical tablet, characterized in that it can be obtained by means of a process comprising at least one step consisting in milling and cutting, and combinations of these steps, at least one pharmaceutical composition, as described above, followed by at least one compression or compacting step and, optionally, by a coating step as also described above.

A subject of the present invention is also a pharmaceutical gelatin capsule, characterized in that it can be obtained by means of a process comprising at least one step consisting in filling with at least one pharmaceutical composition, after a milling step, a cutting step or a combination of these steps, and optionally, a coating step, as described above.

A subject of the present invention is also a molded pharmaceutical tablet, characterized in that it consists of a pharmaceutical composition obtained by means of an injection-molding device, optionally followed by a coating step, as described above.

Finally, the present invention also relates to the use of polydextrose for the production, by extrusion or injection molding, of a pharmaceutical composition comprising a solid dispersion of at least one active principle in a pharmaceutically acceptable polymer matrix, said polymer matrix comprising a blend of polydextrose, in the form of a continuous polydextrose phase, and at least one polymer other than polydextrose, in the form of a continuous phase of this polymer, the proportion of said polydextrose being at least 20% by weight and the proportion of said at least one polymer other than polydextrose being at least 20% by weight, relative to the total weight of said polymer matrix.

The following examples are intended to illustrate the present invention and should in no way be interpreted as being able to limit the scope thereof.

Unless otherwise specified, the percentages by weight indicated in the examples are percentages by weight expressed relative to the total weight.

In the following text, the term "active principle A" is intended to mean the active principle N-piperidino-5-(4-bromophenyl)-1-(2,4-dichlorophenyl)-4-methylpyrazole-3-carboxamide.

Example 1

Molded Tablet with a Polydextrose and Copovidone (50:50) Polymer Matrix and 0.5% of Active Principle A physical mixture containing 0.5% by weight of active principle A, 49.75% by weight of copovidone sold under the name Kollidon VA 64® by the company BASF and 49.75% by weight of polydextrose sold by the company Danisco under the name Litesse Ultra® is prepared. The physical mixing is carried out at ambient temperature (approximately 25° C.) using a Turbula® mixer, for 45 minutes, so as to obtain a homogeneous physical mixture.

An injection-molding machine from the company Erinca, model Sprinter 11, is fed with this physical mixture. The operating parameters are as follows:
barrel temperature of the first heating zone: 120° C.;
barrel temperature of the second heating zone: 140° C.;
nozzle temperature: 160° C.;
hot runner temperature: 160° C.

The mold used is such that it makes it possible to obtain a molded tablet having a size and shape substantially identical to those of a gelatin capsule of size 0.

After cooling to ambient temperature, the molded tablets with a polydextrose and copovidone polymer matrix thus obtained (polydextrose:copovidone weight ratio of 50:50) have an average mass of 1053 mg, each molded tablet containing a dose of approximately 5 mg of active principle A.

Comparative Example 1

Molded Tablet with a Copovidone Polymer Matrix and with 0.5% of Active Principle A physical mixture containing 0.5% by weight of active principle A and 99.5% by weight of copovidone sold under the name Kollidon VA 64®, by the company BASF is prepared. The physical mixing is carried out at ambient temperature (approximately 25° C.) using a Turbula mixer, for 60 minutes, so as to obtain a homogeneous physical mixture.

An injection-molding machine from the company Erinca, model Sprinter 11, is fed with this physical mixture. The operating parameters are as follows:
barrel temperature of the first heating zone: 120° C.;
barrel temperature of the second heating zone: 150° C.;
nozzle temperature: 160° C.;
hot runner temperature: 160° C.

The mold used is such that it makes it possible to obtain a molded tablet having a size and shape substantially identical to those of a gelatin capsule of size 0.

After cooling to ambient temperature, the molded tablets with a copovidone polymer matrix thus obtained have an average mass of 939 mg, each molded tablet containing a dose of 5 mg of active principle A.

Comparative Example 2

Molded Tablet with a Polydextrose Polymer Matrix and with 0.5% of Active Principle A physical mixture containing 0.5% by weight of active principle A and 99.5% by weight of polydextrose sold by the company Danisco under the name Litesse Ultra® is prepared. The physical mixing is carried out at ambient temperature (approximately 25° C.) using a Turbula® mixer, for 45 minutes, so as to obtain a homogeneous physical mixture.

An injection-molding machine from the company Erinca, model Sprinter 11, is fed with this physical mixture. The operating parameters are as follows:
barrel temperature of the first heating zone: 120° C.;
barrel temperature of the second heating zone: 155° C.;
nozzle temperature: 160° C.;
hot runner temperature: 160° C.

The mold used is such that it makes it possible to obtain a molded tablet having a size and shape substantially identical to those of a gelatin capsule of size 0.

After cooling to ambient temperature, the molded tablets with a polydextrose polymer matrix thus obtained have an average mass of 1150 mg, each molded tablet containing a dose of approximately 5 mg of active principle A.

Example 2

In vitro Dissolution Tests

The dissolution of the active principle A, using the molded tablets prepared in example 1 and in comparative examples 1 and 2 above, is studied.

The dissolution kinetics are measured in paddle devices, with a simulated gastro-intestinal dissolution medium at pH 6.5, composed of a mixture of a quarter of a volume of simulated gastric medium without enzymes according to the Pharmacopeia USP XXI (2 g/liter of sodium chloride, the pH of which is adjusted to pH=1.2 with 11.6 M hydrochloric acid) and three quarters of a volume of the simulated intestinal medium without enzymes according to the Pharmacopeia USP XXI (6.8 g/liter of monopotassium phosphate, the pH of which is adjusted to 7.5 with 10 M sodium hydroxide), at 37° C. and with paddle stirring at 75 rpm. The concentration of active principle A dissolved in the dissolution medium is determined by taking a sample of 1 ml at the indicated time, each sample being filtered through a 5 μm membrane and then assayed by liquid chromatography.

Three measurements are taken each time, in order to deduce therefrom a mean value of percentage dissolution for a given time.

The results (means) are reported in the following table 1. They are expressed as percentage of active principle A dissolved, at a rate of 2 molded tablets per bowl containing 500 ml of dissolution medium.

TABLE 1 dissolution of active principle A using the molded tablets with a copovidone and/or polydextrose polymer matrix % dissolution of active principle A (means of 3 measurements)

| Time (min) | Molded tablets of comparative example 1 (copovidone polymer matrix) | Molded tablets of comparative example 2 (polydextrose polymer matrix) | Molded tablets of example 1 (50:50 copovidone and polydextrose polymer matrix) |
|---|---|---|---|
| 15 | 22 | 48.67 | 37.33 |
| 30 | 40.67 | 55.50 | 62.50 |
| 60 | 66.83 | 57.50 | 86.83 |
| 120 | 84.17 | 53.33 | 90.50 |
| 180 | 84.17 | 52.17 | 90.83 |
| 240 | 84.50 | 47.50 | 89.83 |

According to these results, the molded tablets with a copovidone and polydextrose (50:50) polymer matrix according to the invention provide a solubility of active principle A, at least from 30 minutes, that is clearly greater than that obtained with each of the molded tablets with a polymer matrix of copovidone alone and the molded tablets with a polymer matrix of polydextrose alone.

Example 3

In vivo Study of Bioavailability molded tablets according to the invention, with a polydextrose and copovidone (50:50) polymer matrix and with 0.5% of active principle, are again prepared, in the following way.

A physical mixture containing 0.5% by weight of active principle A, 49.75% by weight of copovidone sold under the name Kollidon VA 64® by the company BASF and 49.75% by weight of polydextrose sold by the company Danisco under the name Litesse Ultra® prepared. The physical mixing is carried out at ambient temperature approximately 25° C.) in 2 stages of 30 minutes, using a Robotainer® mixer, so as to obtain a homogeneous physical mixture.

An injection-molding machine from the company Erinca, model Sprinter 11, is fed with this physical mixture. The operating parameters are as follows:
  barrel temperature of the first heating zone: 120° C.;
  barrel temperature of the second heating zone: 140° C.;
  nozzle temperature: 160° C.;
  hot runner temperature: 160° C.
The mold used is such that it makes it possible to obtain a molded tablet having a size and shape substantially identical to those of a gelatin capsule of size 0.

After cooling to ambient temperature, the molded tablets with a polydextrose and copovidone polymer matrix (polydextrose:copovidone weight ratio of 50:50) thus obtained have an average mass of 1084 mg, each molded tablet containing a dose of approximately 5 mg of active principle A.

In vivo Study

The bioavailability of a dose of 10 mg of active principle A is studied on 12 young normal male volunteers. The dose of 10 mg of active principle A is composed of 2 molded tablets of 5 mg prepared as described above in this Example 3.

A control gelatin capsule manufactured by means of a wet granulation process is also used as a reference in this trial, said gelatin capsule having the following unit composition:

TABLE 2 composition of the control gelatin capsule

| Active principle A | 5 mg |
|---|---|
| Corn starch | 80 mg |
| Lactose monohydrate | 279 mg |
| Hypromellose | 10 mg |
| Sodium lauryl sulfate | 2 mg |
| Sodium croscarmellose | 20 mg |
| Magnesium stearate | 4 mg |
| Orange gelatin capsule size 0 | 1 |

The dose of 10 mg of active principle A is composed of 2 control gelatin capsules 20 of 5 mg.

The study comprises 4 periods of oral administrations, 7 days apart. Blood samples are taken from each individual before oral administration and then 0.5; 1; 1.5; 2; 2.5; 3; 4; 6; 8; 12; 24; 36; 48; 72; 120 and 168 hours after administration. For each sample taken, the content of active principle A is determined by means of a validated LC-MS/MS method with a quantification limit at 1 ng/ml. For each administration, the bioavailability of active principle A is determined by measuring the AUC calculated between 0 and 120 hours after administration in ng.h/ml. The means of the results obtained are reported in the following table 3.

TABLE 3

In vivo study of bioavailability

| Pharmaceutical form | C max (ng/ml) | T max (h) | $AUC_{0-120}$ (ng · h/ml) |
|---|---|---|---|
| Molded tablet of Example 3 | 134 | 1.5 | 1408 |
| Control gelatin capsule | 41 | 1.5 | 906 |

It emerges from the results of this study that, on an empty stomach, the molded tablet according to the invention (Example 3) gives an AUC, and therefore a bioavailability of active principle A, 1.55 times greater than that obtained with the control gelatin capsule.

Example 4

Function of the Polydextrose—In vitro Disintegration Tests 4.1 Copovidone and Polydextrose Matrix—In vitro Disintegration Tests The following preparations 1 to 7 (without active principle) are prepared.

Preparation 1: Molded Tablet with a Copovidone Polymer Matrix

An injection-molding machine from the company Erinca, model Sprinter 11, is fed with copovidone sold under the name Kollidon® VA 64 by the company BASF. The operating parameters are as follows:

barrel temperature of the first heating zone: 130° C.;
barrel temperature of the second heating zone: 139° C.;
nozzle temperature: 141° C.;
hot runner temperature: 170° C.

The mold used is such that it makes it possible to obtain a molded tablet having a size and shape substantially identical to those of a gelatin capsule of size 0.

After cooling to ambient temperature, the molded tablets with a copovidone polymer matrix thus obtained have an average mass of 988 mg.

Preparation 2: Molded Tablet with a Polydextrose and Copovidone (20:80) Polymer Matrix A physical mixture containing 80% by weight of copovidone sold under the name Kollidon® VA 64 by the company BASF and 20% by weight of polydextrose sold by the company Danisco under the name Litesse Ultra® is prepared. The physical mixing is carried out at ambient temperature (approximately 25° C.) using a Turbula® mixer, for 45 minutes, so as to obtain a homogeneous physical mixture.

An injection-molding machine from the company Erinca, model Sprinter 11, is fed with this mixture. The operating parameters are as follows:
barrel temperature of the first heating zone: 130° C.;
barrel temperature of the second heating zone: 140° C.;
nozzle temperature: 160° C.;
hot runner temperature: 160° C.

The mold used is such that it makes it possible to obtain a molded tablet having a size and shape substantially identical to those of a gelatin capsule of size 0.

After cooling to ambient temperature, the molded tablets with a polydextrose and copovidone polymer matrix (polydextrose:copovidone weight ratio of 20:80) thus obtained have an average mass of 1002 mg.

Preparation 3: Molded Tablet with a Polydextrose and Copovidone (33:67) Polymer Matrix A physical mixture containing 67% by weight of copovidone sold under the name Kollidon® VA 64 by the company BASF and 33% by weight of polydextrose sold by the company Danisco under the name Litesse Ultra® is prepared. The physical mixing is carried out at ambient temperature (approximately 25° C.) using a Turbula® mixer, for 35 minutes, so as to obtain a homogeneous physical mixture.

An injection-molding machine from the company Erinca, model Sprinter 11, is fed with this mixture. The operating parameters are as follows:
barrel temperature of the first heating zone: 130° C.;
barrel temperature of the second heating zone: 140° C.;
nozzle temperature: 160° C.;
hot runner temperature: 160° C.

The mold used is such that it makes it possible to obtain a molded tablet having a size and shape substantially identical to those of a gelatin capsule of size 0.

After cooling to ambient temperature, the molded tablets with a polydextrose and copovidone polymer matrix (polydextrose:copovidone weight ratio of 33:67) thus obtained have an average mass of 1034 mg.

Preparation 4: Molded Tablet with a Polydextrose and Copovidone (50:50) Polymer Matrix A physical mixture containing 50% by weight of copovidone sold under the name Kollidon® VA 64 by the company BASF and 50% by weight of polydextrose sold by the company Danisco under the name Litesse Ultra® is prepared. The physical mixing is carried out at ambient temperature (approximately 25° C.) using a Turbula® mixer, for 40 minutes, so as to obtain a homogeneous physical mixture.

An injection-molding machine from the company Erinca, model Sprinter 11, is fed with this mixture. The operating parameters are as follows:
barrel temperature of the first heating zone: 120° C.;
barrel temperature of the second heating zone: 140° C.;
nozzle temperature: 160° C.;
hot runner temperature: 160° C.

The mold used is such that it makes it possible to obtain a molded tablet having a size and shape substantially identical to those of a gelatin capsule of size 0.

After cooling to ambient temperature, the molded tablets with a polydextrose and copovidone polymer matrix (polydextrose:copovidone weight ratio of 50:50) thus obtained have an average mass of 1117 mg.

Preparation 5: Molded Tablet with a Polydextrose and Copovidone (67:33) Polymer Matrix A physical mixture containing 33% by weight of copovidone sold under the name Kollidon® VA 64 by the company BASF and 67% by weight of polydextrose sold by the company Danisco under the name Litesse Ultra® is prepared. The physical mixing is carried out at ambient temperature (approximately 25° C.) using a Turbulae mixer, for 40 minutes, so as to obtain a homogeneous physical mixture.

An injection-molding machine from the company Erinca, model Sprinter 11, is fed with this mixture. The operating parameters are as follows:
barrel temperature of the first heating zone: 130° C.;
barrel temperature of the second heating zone: 140° C.;
nozzle temperature: 160° C.;
hot runner temperature: 160° C.

The mold used is such that it makes it possible to obtain a molded tablet having a size and shape substantially identical to those of a gelatin capsule of size 0.

After cooling to ambient temperature, the molded tablets with a polydextrose and copovidone polymer matrix (polydextrose:copovidone weight ratio of 67:33) thus obtained have an average mass of 1099 mg.

Preparation 6: Molded Tablet with a Polydextrose and Copovidone (80:20) Polymer Matrix A physical mixture containing 20% by weight of copovidone sold under the name Kollidon® VA 64 by the company BASF and 80% by weight of polydextrose sold by the company Danisco under the name Litesse Ultra® is prepared. The physical mixing is carried out at ambient temperature (approximately 25° C.) using a Turbula® mixer, for 120 minutes, so as to obtain a homogeneous physical mixture.

An injection-molding machine from the company Erinca, model Sprinter 11, is fed with this mixture. The operating parameters are as follows:
barrel temperature of the first heating zone: 130° C.;
barrel temperature of the second heating zone: 140° C.;
nozzle temperature: 160° C.;
hot runner temperature: 160° C.

The mold used is such that it makes it possible to obtain a molded tablet having a size and shape substantially identical to those of a gelatin capsule of size 0.

After cooling to ambient temperature, the molded tablets with a polydextrose and copovidone polymer matrix (polydextrose:copovidone weight ratio of 80:20) thus obtained have an average mass of 1144 mg.

Preparation 7: Molded Tablet with a Polydextrose Polymer Matrix

An injection-molding machine from the company Erinca, model Sprinter 11, is fed with polydextrose sold by the company Danisco under the name Litesse Ultra®. The operating parameters are as follows:
barrel temperature of the first heating zone: 120° C.;

barrel temperature of the second heating zone: 145° C.;
nozzle temperature: 150° C.;
hot runner temperature: 160° C.

The mold used is such that it makes it possible to obtain a molded tablet having a size and shape substantially identical to those of a gelatin capsule of size 0.

After cooling to ambient temperature, the molded tablets with a polydextrose polymer matrix thus obtained have an average mass of 1186 mg.

In vitro Test for Disintegration of the Molded Tablets with a Copovidone and Polydextrose Matrix The ability of the molded tablets with a polydextrose and/or copovidone polymer matrix, of preparations 1 to 7 above, to disintegrate in demineralized water, as disintegration medium, at a temperature of 37+/−2° C. is studied according to the conditions of the disintegration test for tablets as described in section 2.9.1. of the European Pharmacopeia.

Three measurements are taken each time in order to deduce therefrom a mean value of disintegration time in minutes.

The results are reported in table 4 below and are the subject of FIG. 1.

TABLE 4

In vitro test for disintegration of the molded tablets with a copovidone and polydextrose matrix

| Molded tablets | % copovidone of the polymer matrix | % polydextrose of the polymer matrix | Disintegration time (mean; in minutes) |
|---|---|---|---|
| Preparation 1 | 100 | 0 | 56.4 |
| Preparation 2 | 80 | 20 | 48 |
| Preparation 3 | 67 | 33 | 35.7 |
| Preparation 4 | 50 | 50 | 29 |
| Preparation 5 | 33 | 67 | 21.3 |
| Preparation 6 | 20 | 80 | 15 |
| Preparation 7 | 0 | 100 | 9.5 |

According to these results, the addition of polydextrose to copovidone, in the form of a blend of two respective continuous phases of these two polymers (not discretely dispersed in one another) makes it possible to decrease the disintegration time of the molded tablets.

4.2 Eudragit® E100 and Polydextrose Matrix—In vitro Disintegration Test

The following preparations 8 to 12 (without active principle) are prepared.

Preparation 8: Molded Tablet with a Polydextrose and Eudragit® E 100 (55:45) Matrix A physical mixture containing 45% by weight of acrylic and methacrylic polymer sold under the name Eudragit® E 100 by the company Röhm, and 55% by weight of polydextrose sold by the company Danisco under the name Litesse Ultra® is prepared. The physical mixing is carried out at ambient temperature (approximately 25° C.) using a Turbula® mixer, for 30 minutes, so as to obtain a homogeneous physical mixture.

An injection-molding machine from the company Erinca, model Sprinter 11, is fed with this mixture. The operating parameters are as follows:
barrel temperature of the first heating zone: 140° C.;
barrel temperature of the second heating zone: 150° C.;
nozzle temperature: 160° C.;
hot runner temperature: 180° C.

The mold used is such that it makes it possible to obtain a molded tablet having a size and shape substantially identical to those of a gelatin capsule of size 0.

After cooling to ambient temperature, the molded tablets with a polydextrose and Eudragit® E 100 polymer matrix (polydextrose:Eudragit® E 100 weight ratio of 55:45) thus obtained have an average mass of 1015 mg.

Preparation 9: Molded Tablet with a Polydextrose and Eudragit® E 100 (60:40) Polymer Matrix A physical mixture containing 40% by weight of acrylic and methacrylic polymer sold under the name Eudragit® E 100 by the company Röhm, and 60% by weight of polydextrose sold by the company Danisco under the name Litesse Ultra® is prepared. The physical mixing is carried out at ambient temperature (approximately 25° C.) using a Turbula® mixer, for 30 minutes, so as to obtain a homogeneous physical mixture.

An injection-molding machine from the company Erinca, model Sprinter 11, is fed with this mixture. The operating parameters are as follows:
barrel temperature of the first heating zone: 140° C.;
barrel temperature of the second heating zone: 150° C.;
nozzle temperature: 160° C.;
hot runner temperature: 180° C.

The mold used is such that it makes it possible to obtain a molded tablet having a size and shape substantially identical to those of a gelatin capsule of size 0.

After cooling to ambient temperature, the molded tablets with a polydextrose and Eudragit® E 100 polymer matrix (polydextrose:Eudragit® E 100 weight ratio of 60:40) thus obtained have an average mass of 1048 mg.

Preparation 10: Molded Tablet with a Polydextrose and Eudragite® E 100 (67:33) Polymer Matrix A physical mixture containing 33% by weight of acrylic and methacrylic polymer sold under the name Eudragit® E 100 by the company Röhm, and 67% by weight of polydextrose sold by the company Danisco under the name Litesse Ultra® is prepared. The physical mixing is carried out at ambient temperature (approximately 250° C.) using a Turbula® mixer, for 60 minutes, so as to obtain a homogeneous physical mixture.

An injection-molding machine from the company Erinca, model Sprinter 11, is fed with this mixture. The operating parameters are as follows:
barrel temperature of the first heating zone: 140° C.;
barrel temperature of the second heating zone: 150° C.;
nozzle temperature: 160° C.;
hot runner temperature: 180° C.

The mold used is such that it makes it possible to obtain a molded tablet having a size and shape substantially identical to those of a gelatin capsule of size 0.

After cooling to ambient temperature, the molded tablets with a polydextrose and Eudragit® E 100 polymer matrix (polydextrose:Eudragit® E 100 weight ratio of 67:33) thus obtained have an average mass of 1057 mg.

Preparation 11: Molded Tablet with a Polydextrose and Eudragit® E 100 (75:25) Polymer Matrix A physical mixture containing 25% by weight of acrylic and methacrylic polymer sold under the name Eudragit® E 100 by the company Röhm, and 75% by weight of polydextrose sold by the company Danisco under the name Litesse Ultra® is prepared. The physical mixing is carried out at ambient temperature (approximately 250° C.) using a Turbula® mixer, for 30 minutes, so as to obtain a homogeneous physical mixture.

An injection-molding machine from the company Erinca, model Sprinter 11, is fed with this mixture. The operating parameters are as follows:
barrel temperature of the first heating zone: 130° C.;
barrel temperature of the second heating zone: 140° C.;

nozzle temperature: 160° C.;
hot runner temperature: 180° C.

The mold used is such that it makes it possible to obtain a molded tablet having a size and shape substantially identical to those of a gelatin capsule of size 0.

After cooling to ambient temperature, the molded tablets with a polydextrose and Eudragit® E 100 polymer matrix (polydextrose:Eudragit® E 100 weight ratio of 75:25) thus obtained have an average mass of 1119 mg.

Preparation 12: Molded Tablet with a Polydextrose and Eudragit® E 100 (90:10) Polymer Matrix A physical mixture containing 10% by weight of acrylic and methacrylic polymer sold under the name Eudragit® E 100 by the company Röhm, and 90% by weight of polydextrose sold by the company Danisco under the name Litesse Ultra® is prepared. The physical mixing is carried out at ambient temperature (approximately 250° C.) using a Turbula® mixer, for 30 minutes, so as to obtain a homogeneous physical mixture.

An injection-molding machine from the company Erinca, model Sprinter 11, is fed with this mixture. The operating parameters are as follows:
barrel temperature of the first heating zone: 130° C.;
barrel temperature of the second heating zone: 140° C.;
nozzle temperature: 160° C.;
hot runner temperature: 180° C.

The mold used is such that it makes it possible to obtain a molded tablet having a size and shape substantially identical to those of a gelatin capsule of size 0.

After cooling to ambient temperature, the molded tablets with a polydextrose and Eudragit®E 100 polymer matrix (polydextrose:Eudragit® E 100 weight ratio of 90:10) thus obtained have an average mass of 1188 mg.

In vitro Test for Disintegration of the Molded Tablets with a Eudragit® E 100 and Polydextrose Matrix The ability of the molded tablets with a polydextrose and/or Eudragit® E 100 polymer matrix, of preparations 7 to 12 above, to disintegrate in demineralized water, as disintegration medium, at a temperature of 37+/−2° C. is studied according to the conditions of the disintegration test for tablets as described in section 2.9.1. of the European Pharmacopeia.

Three measurements are taken each time in order to deduce therefrom a mean value of disintegration time in minutes.

Figure 2:
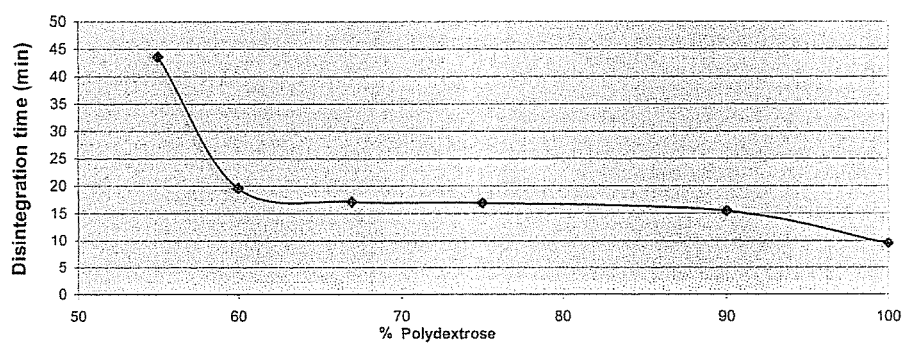
FIG. 2 is a curve showing the disintegration time (in minutes) of molded tablets (preparations 7 to 12), as a function of the percentage of polydextrose in a polydextrose and Eudragit E 100 polymer matrix, expressed relative to the total weight of this polymer matrix, according to the in vitro disintegration test (section 4.2 of example 4; table 5).

The results are reported in table 5 below and are the subject of FIG. 2.

TABLE 5

In vitro test for disintegration of the molded tablets with a Eudragit ® E 100 and polydextrose matrix

| Molded tablets | % Eudragit ® E 100 of the polymer matrix | % polydextrose of the polymer matrix | Disintegration time (mean; in minutes) |
|---|---|---|---|
| Preparation 8 | 45 | 55 | 43.6 |
| Preparation 9 | 40 | 60 | 19.6 |
| Preparation 10 | 33 | 67 | 17.1 |
| Preparation 11 | 25 | 75 | 16.9 |
| Preparation 12 | 10 | 90 | 15.4 |
| Preparation 7 | 0 | 100 | 9.5 |

According to these results, the addition of polydextrose to Eudragit® E 100, in the form of a blend of two respective continuous phases of these two polymers (not discretely dispersed in one another) makes it possible to decrease the disintegration time of the molded tablets.

4.3 Aqoat® ASMG and Polydextrose Matrix—In vitro Disintegration Test

The following preparations 13 to 15 (without active principle) are prepared.

Preparation 13: Molded Tablet with a Polydextrose and Aqoat® ASMG (75:25) Polymer Matrix A physical mixture containing 25% by weight of hydroxypropylmethylcellulose acetate succinate, sold under the name Aqoat®ASMG by the company Shin-Etsu, and 75% by weight of polydextrose sold by the company Danisco under the name Litesse Ultra® is prepared. The physical mixing is carried out at ambient temperature (approximately 250° C.) using a Turbula® mixer, for 40 minutes, so as to obtain a homogeneous physical mixture.

An injection-molding machine from the company Erinca, model Sprinter 11, is fed with this mixture. The operating parameters are as follows:
barrel temperature of the first heating zone: 125° C.;
barrel temperature of the second heating zone: 145° C.;
nozzle temperature: 160° C.;
hot runner temperature: 170° C.

The mold used is such that it makes it possible to obtain a molded tablet having a size and shape substantially identical to those of a gelatin capsule of size 0.

After cooling to ambient temperature, the molded tablets with a polydextrose and Aqoat® ASMG polymer matrix (polydextrose:Aqoat® ASMG weight ratio of 75:25) thus obtained have an average mass of 1182 mg.

Preparation 14: Molded Tablet with a Polydextrose and Aqoat® ASMG (80:20) Polymer Matrix A physical mixture containing 20% by weight of hydroxypropylmethylcellulose acetate succinate, sold under the name Aqoat®ASMG by the company Shin-Etsu, and 80% by weight of polydextrose sold by the company Danisco under the name Litesse Ultra® is prepared. The physical mixing is carried out at ambient temperature (approximately 250° C.) using a Turbula® mixer, for 40 minutes, so as to obtain a homogeneous physical mixture.

An injection-molding machine from the company Erinca, model Sprinter 11, is fed with this mixture. The operating parameters are as follows:
barrel temperature of the first heating zone: 130° C.;
barrel temperature of the second heating zone: 140° C.;
nozzle temperature: 145° C.;
hot runner temperature: 150° C.

The mold used is such that it makes it possible to obtain a molded tablet having a size and shape substantially identical to those of a gelatin capsule of size 0.

After cooling to ambient temperature, the molded tablets with a polydextrose and Aqoat® ASMG polymer matrix (polydextrose:Aqoate ASMG weight ratio of 80:20) thus obtained have an average mass of 1101 mg.

Preparation 15: Molded Tablet with a Polydextrose and Aqoat® ASMG (85:15) Polymer Matrix A physical mixture containing 15% by weight of hydroxypropylmethylcellulose acetate succinate, sold under the name Aqoat®ASMG by the company Shin-Etsu, and 85% by weight of polydextrose sold by the company Danisco under the name Litesse Ultra® is prepared. The physical mixing is carried out at ambient temperature (approximately 25° C.) using a Turbula® mixer, for 40 minutes, so as to obtain a homogeneous physical mixture.

An injection-molding machine from the company Erinca, model Sprinter 11, is fed with this mixture. The operating parameters are as follows:
barrel temperature of the first heating zone: 130° C.;
barrel temperature of the second heating zone: 140° C.;

nozzle temperature: 145° C.;
hot runner temperature: 150° C.

The mold used is such that it makes it possible to obtain a molded tablet having a size and shape substantially identical to those of a gelatin capsule of size 0.

After cooling to ambient temperature, the molded tablets with a polydextrose and Aqoat® ASMG polymer matrix (polydextrose:Aqoat® ASMG weight ratio of 85:15) thus obtained have an average mass of 1122 mg.

In vitro Test for Disintegration of the Molded Tablets with a Hydroxypropylmethylcellulose Acetate Succinate (Aqoat® ASMG) and Polydextrose Matrix The ability of the molded tablets with a polydextrose and/or Aqoat® ASMG polymer matrix, of preparations 7 and 13 to 15 above, to disintegrate in demineralized water, as disintegration medium, at a temperature of 37+/−20° C. is studied according to the conditions of the disintegration test for tablets as described in section 2.9.1. of the European Pharmacopeia.

Three measurements are taken each time in order to deduce therefrom a mean value of disintegration time in minutes.

Figure 3:
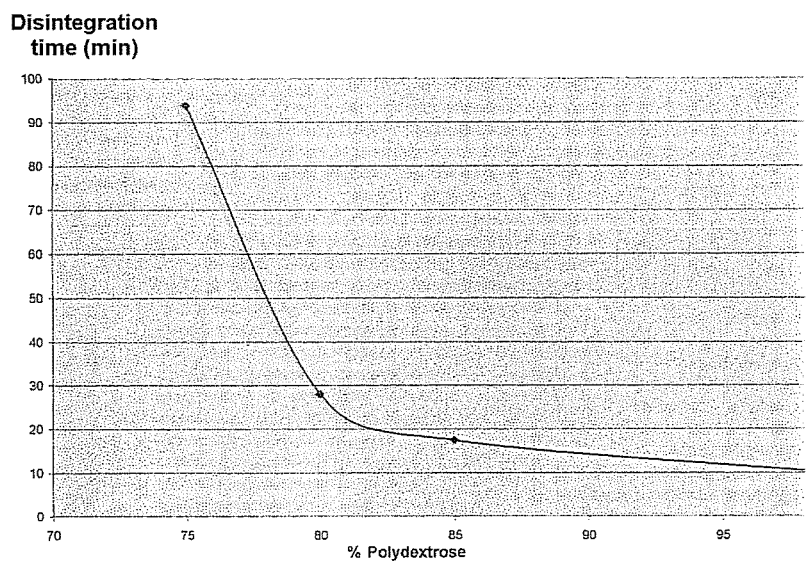
FIG. 3 is a curve showing the disintegration time (in minutes) of molded tablets (preparations 7 and 13 to 15), as a function of the percentage of polydextrose in a polydextrose and Aqoat ASMG polymer matrix, expressed relative to the total weight of this polymer matrix, according to the in vitro disintegration test (section 4.3 of example 4; table 6).

The results are reported in table 6 below and are the subject of FIG. 3.

TABLE 6

In vitro test for disintegration of the molded tablets with a hydroxypropylmethylcellulose acetate succinate and polydextrose matrix

| Molded tablets | % Aqoat ® ASMG of the polymer matrix | % polydextrose of the polymer matrix | Disintegration time (mean; in minutes) |
| --- | --- | --- | --- |
| Preparation 13 | 25 | 75 | 93.8 |
| Preparation 14 | 20 | 80 | 28 |
| Preparation 15 | 15 | 85 | 17.4 |
| Preparation 7 | 0 | 100 | 9.5 |

According to these results, the addition of polydextrose to Aqoat® ASMG, in the form of a blend of two respective continuous phases of these two polymers (not discretely dispersed in one another) makes it possible to decrease the disintegration time of the molded tablets.

4.4 Hydroxypropylcellulose and Polydextrose Matrix

The following preparations 16 to 18 (without active principle) are prepared.

Preparation 16: Molded Tablet with a Polydextrose and Hydroxypropylcellulose Polymer Matrix (50:50; with 2% by Weight of Vitamin E Polyethylene Glycol Succinate)

A physical mixture containing 49% by weight of hydroxypropylcellulose, such as that sold under the name Klucel® EF by the company Aqualon; 49% by weight of polydextrose sold by the company Danisco under the name Litesse Ultra®; and 2% by weight of vitamin E polyethylene glycol succinate as sold by the company Eastman under the name Eastman® Vitamin E TPGS is prepared. The physical mixing is carried out at a temperature of approximately 50° C. using a Rayneri reverse propeller blade mixer, for approximately 15 minutes, so as to obtain a homogeneous physical mixture.

An injection-molding machine from the company Erinca, model Sprinter 11, is fed with this mixture. The operating parameters are as follows:
barrel temperature of the first heating zone: 125° C.;
barrel temperature of the second heating zone: 146° C.;
nozzle temperature: 155° C.;
hot runner temperature: 160° C.

The mold used is such that it makes it possible to obtain a molded tablet having a size and shape substantially identical to those of a gelatin capsule of size 0.

After cooling to ambient temperature, the molded tablets with a polydextrose, hydroxypropylcellulose and vitamin E polyethylene glycol succinate polymer matrix (polydextrose:hydroxypropylcellulose weight ratio of 50:50) thus obtained have an average mass of 1051 mg.

Preparation 17: Molded Tablet with a Polydextrose and Hydroxypropylcellulose Polymer Matrix (67:33, with 2% by Weight of Vitamin E Polyethylene Glycol Succinate)

A physical mixture containing 32.3% by weight of hydroxypropylcellulose, such as that sold under the name Klucel® EF by the company Aqualon; 65.7% by weight of polydextrose sold by the company Danisco under the name Litesse Ultra®; and 2% by weight of vitamin E polyethylene glycol succinate as sold by the company Eastman under the name Eastman® Vitamin E TPGS is prepared. The physical mixing is carried out at a temperature of approximately 50° C. using a Rayneri reverse propeller blade mixer, for approximately 15 minutes, so as to obtain a homogeneous physical mixture.

An injection-molding machine from the company Erinca, model Sprinter 11, is fed with this mixture. The operating parameters are as follows:
barrel temperature of the first heating zone: 130° C.;
barrel temperature of the second heating zone: 140° C.;
nozzle temperature: 150° C.;
hot runner temperature: 150° C.

The mold used is such that it makes it possible to obtain a molded tablet having a size and shape substantially identical to those of a gelatin capsule of size 0.

After cooling to ambient temperature, the molded tablets with a polydextrose, hydroxypropylcellulose and vitamin E polyethylene glycol succinate polymer matrix (polydextrose:hydroxypropylcellulose weight ratio of 67:33) thus obtained have an average mass of 1126 mg.

Preparation 18: Molded Tablet with a Polydextrose and Hydroxypropylcellulose Polymer Matrix (80:20; with 2% by Weight of Vitamin E Polyethylene Glycol Succinate)

A physical mixture containing 19.6% by weight of hydroxypropylcellulose, such as that sold under the name Klucel®EF by the company Aqualon; 78.4% by weight of polydextrose sold by the company Danisco under the name Litesse Ultra®; and 2% by weight of vitamin E polyethylene glycol succinate as sold by the company Eastman under the name Eastman® Vitamin E TPGS is prepared. The physical mixing is carried out at a temperature of approximately 50° C. using a Rayneri reverse propeller blade mixer, for approximately 15 minutes, so as to obtain a homogeneous physical mixture.

An injection-molding machine from the company Erinca, model Sprinter 11, is fed with this mixture. The operating parameters are as follows:
barrel temperature of the first heating zone: 130° C.;
barrel temperature of the second heating zone: 140° C.;
nozzle temperature: 150° C.;
hot runner temperature: 150° C.

The mold used is such that it makes it possible to obtain a molded tablet having a size and shape substantially identical to those of a gelatin capsule of size 0.

After cooling to ambient temperature, the molded tablets with a polydextrose, hydroxypropylcellulose and vitamin E polyethylene glycol succinate polymer matrix (polydextrose:hydroxypropylcellulose weight ratio of 80:20) thus obtained have an average mass of 1146 mg.

In vitro Tests for Disintegration of the Molded Tablets with a Hydroxypropylcellulose (Klucel® EF ) and Polydextrose Matrix The ability of the molded tablets with a polydextrose and/or Klucel® EF polymer matrix, of preparations 7 and 16 to 18 above, to disintegrate in demineralized water, as disintegration medium, at a temperature of 37+/−2° C. is studied according to the conditions of the disintegration test for tablets as described in section 2.9.1. of the European Pharmacopeia.

Three measurements are taken each time in order to deduce therefrom a mean value of disintegration time in minutes.

Figure 4:
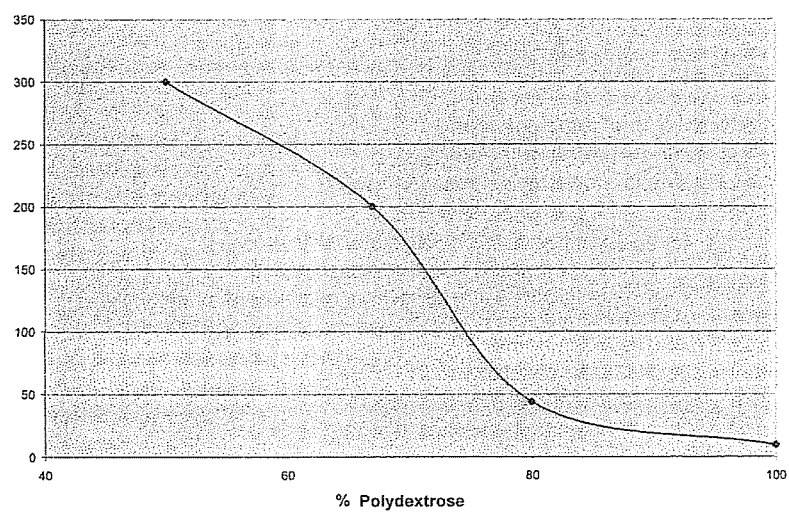
FIG. 4 is a curve showing the disintegration time (in minutes) of molded tablets (preparations 7 and 16 to 18), as a function of the percentage of polydextrose in a polydextrose and Klucel EF polymer matrix, expressed relative to the total weight of this polymer matrix, according to the in vitro disintegration test (section 4.4 of example 4; table 7).

The results are reported in table 7 below and are the subject of FIG. 4.

TABLE 7

In vitro test for disintegration of the molded tablets with a hydroxypropylcellulose and polydextrose matrix

| Molded tablets | % Klucel ® EF of the polymer matrix | % polydextrose of the polymer matrix | Disintegration time (mean; in minutes) |
|---|---|---|---|
| Preparation 16 | 50 | 50 | 300 |
| Preparation 17 | 33 | 67 | 200 |
| Preparation 18 | 20 | 80 | 44 |
| Preparation 7 | 0 | 100 | 9.5 |

According to these results, the addition of polydextrose to hydroxypropylcellulose Klucel® EF, in the form of a blend of two respective continuous phases of these two polymers (not discretely dispersed in one another) makes it possible to decrease the disintegration time of the molded tablets.

Example 5

Solid-state NMR Analyses of the Proton Relaxation Times of the Molded Tablets with a Polydextrose and Copovidone Matrix The following preparation 19 (without active principle) is also prepared.

Preparation 19: Molded Tablet with a Copovidone Polymer Matrix

An injection-molding machine from the company Erinca, model Sprinter 11, is fed with copovidone sold under the name Kollidon VA 64® by the company BASF. The operating parameters are as follows:
 barrel temperature of the first heating zone: 120° C.;
 barrel temperature of the second heating zone: 160° C.;
 nozzle temperature: 160° C.;
 hot runner temperature: 170° C.

The mold used is such that it makes it possible to obtain a molded tablet having a size and shape substantially identical to those of a gelatin capsule of size 0.

After cooling to ambient temperature, the molded tablets with a copovidone polymer matrix thus obtained have an average mass of 972 mg.

Solid-State NMR Analyses

Figure 5:
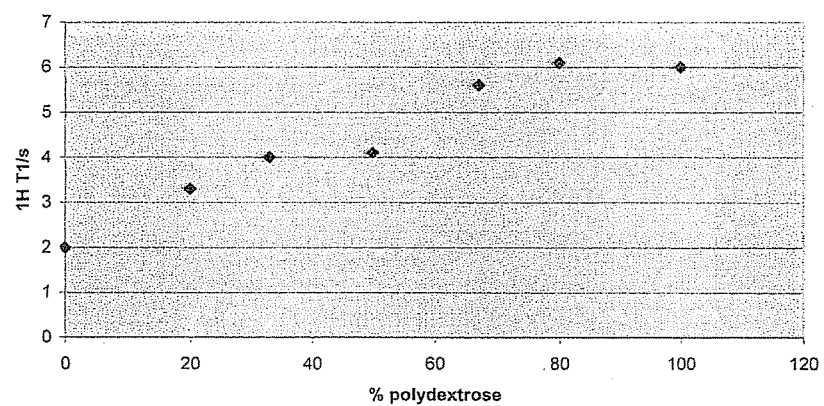
FIG. 5 is a series of points showing the values of the proton relaxation time (T1; in seconds) of the molded tablets with a polydextrose and copovidone matrix (preparations 19 and 2 to 7) as described in example 5.
Figure 6:
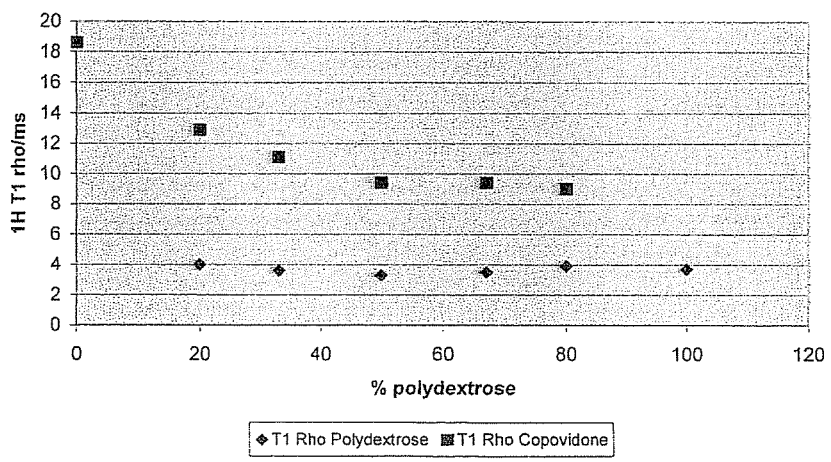
FIG. 6 represents two series of points, each showing the values of the proton relaxation time (T1 Rho; in milliseconds) of the molded tablets with a polydextrose and copovidone matrix (preparations 19 and 2 to 7) as described in example 5. The series of points in the form of diamonds corresponds to the values of the polydextrose relaxation times (T1 Rho) and the series of points in the form of squares corresponds to the values of the copovidone relaxation times (T1 Rho).

The solid-state NMR measurements of the proton relaxation times T1 and T1 Rho, of the molded tablets with a copovidone and/or polydextrose matrix of preparations 2 to 7 and 19 above, are reported in table 8 hereinafter. These results are the subject of FIG. 5 for the representation of T1 in seconds, as a function of the percentage of polydextrose contained in the matrix, and of FIG. 6 for the representation of T1 Rho in milliseconds, as a function of the percentage of polydextrose contained in the matrix.

The solid-state NMR measurements of the proton relaxation times T1 and T1 Rho were carried out according to the method described in the article "Investigation of the physical stability of amorphous drug and drug polymer melts using variable temperature solid state NMR" by A. Forster et al. published in Pharmazie Vol. 58 (2003) pages 761 to 762; but at constant temperature and while varying the respective amounts of polydextrose and of copovidone in the polymeric matrix. Each of the values described is the mean of the results obtained after 3 trials.

According to these results (see FIG. 5), for each polydextrose and copovidone blend, a single proton relaxation value is obtained: $T_1$ (expressed in seconds), which means that it is not possible to differentiate the copovidone and polydextrose phases together, on a scale of 50 nm (measurement sensitivity). In other words, it is not possible to distinguish a discrete domain, of one phase dispersed in the other, the size of which would be greater than 50 nm. Neither of the two polydextrose and copovidone phases is therefore discontinuous on this scale, which corresponds to a macromolecular scale for these two polymers. It is also noted that the value of T1 varies with the composition of the matrix and reflects the proportion of polydextrose present in the matrix.

TABLE 8 values of the proton relaxation times (T1 in seconds and T1 Rho in milliseconds) of the molded tablets with a polydextrose and copovidone matrix

| Molded tablets | % polydextrose of the polymer matrix | % copovidone of the polymer matrix | T1 (s) | T1 Rho polydextrose (ms) | T1 Rho copovidone (ms) |
|---|---|---|---|---|---|
| Preparation 19 | 0 | 100 | 2.0 | — | 18.6 |
| Preparation 2 | 20 | 80 | 3.3 | 4.0 | 12.9 |
| Preparation 3 | 33 | 67 | 4.0 | 3.6 | 11.1 |
| Preparation 4 | 50 | 50 | 4.1 | 3.3 | 9.4 |
| Preparation 5 | 67 | 33 | 5.6 | 3.5 | 9.4 |
| Preparation 6 | 80 | 20 | 6.1 | 3.9 | 9 |
| Preparation 7 | 100 | 0 | 6.0 | 3.7 | — |

After these results (see FIG. 6), for each polydextrose and copovidone blend, two proton relaxation values are obtained: $T_1$ Rho (expressed in milliseconds), which means that it is possible to differentiate two distinct phases on a measuring scale of between 5 nm and 50 nm, which corresponds to the molecular scale for the polydextrose and the copovidone. These results also indicate the composition of the two phases observed. The T1 Rho attributed to the polydextrose remains substantially constant independently of the composition of the matrix analyzed, which indicates that one of the phases consists exclusively of polydextrose. The T1 Rho attributed to the copovidone varies with the composition of the matrix analyzed, up until the matrix contains 50% of polydextrose, then remains constant for polydextrose proportions greater than 50%. This means that the copovidone phase solubilizes polydextrose up to saturation (50% of polydextrose). Two polymer phases therefore coexist on the molecular scale for these two blended and molten polymers, one phase consisting of polydextrose alone, the other polymer phase being a solid solution of polydextrose in the copovidone.

These results therefore prove that:
on the macromolecular scale, no discrete phase of one polymer dispersed in another exists (T1 has a single value), the matrix is therefore continuous;
the molded tablets with a polydextrose and copovidone matrix consist of two polymer phases that are distinct on the molecular level, one phase of polydextrose alone and one polymer phase consisting of a solid solution of polydextrose in copovidone;
on the molecular scale, the phase consisting of the polydextrose alone is continuous (no variation in the T1 Rho attributed to the polydextrose, as a function of the composition of the matrix).

In conclusion, the molded tablets with matrices consisting of a blend of molten polydextrose and copovidone do not contain any discontinuous structures and they consist of two distinct polymer phases, one of which (the phase of polydextrose alone) is continuous. It can therefore be deduced from this that the other phase, consisting of a solid solution of polydextrose in copovidone, is therefore itself also continuous. The molded tablets with a polydextrose and copovidone matrix consist of two distinct and continuous phases, their physical structure is therefore bicontinuous.

Example 6

Molded Tablet with a Polydextrose and Copovidone (20:80) Polymer Matrix Containing 12.41% by Weight of the Active Principle isopropyl 2-butyl-3-[4-[3-(dibutylamino)propyl]benzoyl]-1-benzofuran-5-carboxylate fumarate A physical mixture containing 12.41% by weight of active principle isopropyl 2-butyl-3-[4-[3-(dibutylamino)propyl]benzoyl]-1-benzofuran-5-carboxylate fumarate, 68.08% by weight of copovidone sold under the name Kollidon VA 64® by the company BASF, 17.51% by weight of polydextrose sold by the company Danisco under the name Litesse Ultra® and 2.00% by weight of vitamin E polyethylene glycol succinate as sold by the company Eastman under the name Eastman® Vitamin E TPGS is prepared. The physical mixing is carried out at a temperature of approximately 50° C. using a Rayneri reverse propeller blade mixer, for approximately 15 minutes, so as to obtain a homogeneous physical mixture.

An injection-molding machine from the company Erinca, model Sprinter 11, is fed with this mixture. The operating parameters are as follows:
barrel temperature of the first heating zone: 130° C.;
barrel temperature of the second heating zone: 140° C.;
nozzle temperature: 140° C.;
hot runner temperature: 140° C.

The mold used is such that it makes it possible to obtain a molded tablet having a size and shape substantially identical to those of a gelatin capsule of size 0.

After cooling to ambient temperature, the molded tablets with a polydextrose and copovidone polymer matrix thus obtained (polydextrose:copovidone weight ratio of 20:80) have an average mass of 969 mg, each molded tablet containing a dose of approximately 100 mg of the active principle isopropyl 2-butyl-3-[4-[3-(dibutylamino)propyl]benzoyl]-1-benzofuran-5-carboxylate fumarate.

A differential enthalpy analysis (a single glass transition temperature, equal to 86° C.) and also an X-ray diffraction study make it possible to conclude that the active principle isopropyl 2-butyl-3-[4-[3-(dibutylamino)propyl]benzoyl]-1-benzofuran-5-carboxylate fumarate is not in crystalline form in this composition (i.e. not detected in crystalline form).

Example 7

Molded Tablet with a Polydextrose and Copovidone (20:80) Polymer Matrix Containing 10.03% by Weight of the Active Principle 7-chloro-N,N,5-trimethyl-4-oxo-3-phenyl-3,5-dihydro-4H-pyridazino[4,5-b]indol-1-acetamide A physical mixture containing 10.03% by weight of active principle 7-chloro-N,N,5-trimethyl-4-oxo-3-phenyl-3,5-dihydro-4H-pyridazino[4,5-b]indol-1-acetamide, 71.97% by weight of copovidone sold under the name Kollidon VA 64® by the company BASF and 17.99% by weight of polydextrose sold by the company Danisco under the name Litesse Ultra® is prepared. The physical mixing is carried out at ambient temperature (approximately 25° C.) using a Turbula® mixer, for 40 minutes, so as to obtain a homogenous physical mixture.

An injection-molding machine from the company Erinca, model Sprinter 11, is fed with this physical mixture. The operating parameters are as follows:
barrel temperature of the first heating zone: 150° C.;
barrel temperature of the second heating zone: 170° C.;
nozzle temperature: 180° C.;
hot runner temperature: 180° C.

The mold used is such that it makes it possible to obtain a molded tablet having a size and shape substantially identical to those of a gelatin capsule of size 0.

After cooling to ambient temperature, the molded tablets with a polydextrose and copovidone polymer matrix thus obtained (polydextrose:copovidone weight ratio of 20:80) have an average mass of 985 mg, each molded tablet containing a dose of approximately 100 mg of the active principle 7-chloro-N,N,5-trimethyl-4-oxo-3-phenyl-3,5-dihydro-4H-pyridazino[4,5-b]indol-1-acetamide.

A differential enthalpy analysis (a single glass transition temperature, at 99° C.) and also an X-ray diffraction study make it possible to note that the active principle 7-chloro-N,N,5-trimethyl-4-oxo-3-phenyl-3,5-dihydro-4H-pyridazino[4,5-b]indol-1-acetamide is not in crystalline form in this composition (i.e. not detected in crystalline form).

What is claimed is:

1. A solid pharmaceutical composition comprising a solid dispersion containing N piperidino-5-(4-bromphenyl)-1-(2,4-dichlorophenyl)-4-methylpyrazole-3-carboxamide and a pharmaceutically acceptable polymer matrix, wherein said pharmaceutically acceptable polymer matrix comprises a blend of (i) 80% by weight polydextrose, in the form of a continuous phase, and (ii) 20% by weight copovidone, in the form of a continuous phase wherein said composition disintegrates in demineralized water at 37° C. in about 15 minutes.

2. The pharmaceutical composition as set forth in claim 1, wherein said composition is prepared by means of a process comprising at least one step consisting of producing the composition containing said at least one active principle, said polydextrose and said at least one polymer other than polydextrose, in a screw mixer and at a mixing temperature of between approximately 50° C. and approximately 250° C.

3. The pharmaceutical composition as set forth in claim 1, wherein said continuous polydextrose phase is present in order to promote the disintegration of the composition in an aqueous medium.

4. The pharmaceutical composition as set forth in claim 2, wherein said continuous polydextrose phase is present in order to promote the disintegration of the composition in an aqueous medium.

5. The pharmaceutical composition as set forth in claim 1, wherein said polydextrose is selected from the group consisting of pharmaceutically acceptable polydextroses having a molecular weight of at most 22 000 g/mol, and blends thereof.

6. The pharmaceutical composition as set forth in claim 2, wherein said polydextrose is selected from the group consisting of pharmaceutically acceptable polydextroses having a molecular weight of at most 22 000 g/mol, and blends thereof.

7. The pharmaceutical composition as set forth in claim 3, wherein said polydextrose is selected from the group consisting of pharmaceutically acceptable polydextroses having a molecular weight of at most 22 000 g/mol, and blends thereof.

8. The pharmaceutical composition as set forth in claim 4, wherein said polydextrose is selected from the group consisting of pharmaceutically acceptable polydextroses having a molecular weight of at most 22 000 g/mol, and blends thereof.

9. The pharmaceutical composition as set forth in claim 1, wherein said pharmaceutically acceptable polymer matrix has a bicontinuous structure essentially consisting of a continuous polydextrose phase and of a continuous phase of copovidone.

10. The pharmaceutical composition as set forth in claim 1, wherein the proportion of said pharmaceutically acceptable polymer matrix is between approximately 50% and approximately 99.9% by weight, relative to the total weight of the composition.

11. The pharmaceutical composition as set forth in claim 1, wherein said N-piperidino-5-(4-bromphenyl)-1-(2,4-dichlorophenyl)-4-methylpyrazole-3-carboxamide is predominantly in the amorphous state in said pharmaceutically acceptable polymer matrix.

12. The pharmaceutical composition as set forth in claim 1, wherein the proportion of said N-piperidino-5-(4-bromphenyl)-1-(2,4-dichlorophenyl)-4-methylpyrazole-3-carboxamide is between approximately 0.1% and approximately 50% by weight, relative to the total weight of the composition.

13. The pharmaceutical composition as set forth in claim 2, wherein said composition produced in a screw mixer further comprises at least one component selected from the group consisting of plasticizers, demolding agents or lubricants, fluidifying agents, antioxidants, preserving agents, dyes, flavorings, sweeteners, wetting agents, buffers, adsorbents, absorption promoters, bioadhesive agents and disintegrating agents and a mixture in any combination thereof.

14. The pharmaceutical composition as set forth in claim 13, wherein said mixing temperature is between approximately 80° C. and approximately 200° C.

15. The pharmaceutical composition as set forth in claim 13, wherein said screw mixer is a twin-screw mixer.

16. The pharmaceutical composition as set forth in claim 13, wherein said screw mixer is an extrusion device.

17. The pharmaceutical composition as set forth in claim 16, wherein said step of mixing in producing said composition in an extrusion device is followed by at least one step consisting in forming an extruded composition, at the temperature of the said step of mixing or after cooling of said extruded composition to a suitable forming temperature, said step is selected from the group consisting of calendering, spinning and cutting, or a combination of these steps.

18. The pharmaceutical composition as set forth in claim 13, wherein said screw mixer is an injection-molding device.

19. The pharmaceutical composition as set forth in claim 18, wherein the composition is obtained by means of a process further comprising, after cooling to a suitable temperature for sufficiently solidifying the composition obtained, at least one step selected from the group consisting of milling and cutting, or a combination of these steps.

20. The pharmaceutical composition as set forth in claim 19, wherein said composition is obtained by means of a process further comprising at least one coating step for modified release.

21. A pharmaceutical tablet obtained by means of a process comprising at least one step consisting of compression or compacting of the pharmaceutical composition as set forth in claim 19.

22. The pharmaceutical tablet as set forth in claim 21, wherein said tablet is obtained by means of a process further comprising at least one coating step for modified release.

23. A pharmaceutical gelatin capsule obtained by means of a process comprising at least one step consisting of filling with the pharmaceutical composition as set forth in claim 19.

24. A pharmaceutical gelatin capsule obtained by means of a process comprising at least one step consisting of filling with the pharmaceutical composition as set forth in claim 20.

25. A molded pharmaceutical tablet comprising a pharmaceutical composition as set forth in claim 18.

26. A molded pharmaceutical tablet comprising a pharmaceutical composition as set forth in claim 20.

* * * * *

UNITED STATES PATENT AND TRADEMARK OFFICE
CERTIFICATE OF CORRECTION

PATENT NO. : 9,084,730 B2  
APPLICATION NO. : 11/686611  
DATED : July 21, 2015  
INVENTOR(S) : Bedos et al.

Page 1 of 1

It is certified that error appears in the above-identified patent and that said Letters Patent is hereby corrected as shown below:

On the Title Page:
Item (57), line 5: replace: "a characterized" with --characterized--.

In the Claims:
Column 28, claim 1, lines 55-56: replace: "N piperidino-5-(4-bromphenyl)-1-(2,4-dichlorophenyl)-4-methylpyrazole-3-carboxamide" with --N-piperidino-5-(4-bromophenyl)-1-(2,4-dichlorophenyl)-4-methylpyrazole-3-carboxamide--;

Column 28, claim 2, line 66: replace: "said at least one active principle" with --N-piperidino-5-(4-bromophenyl)-1-(2,4-dichlorophenyl)-4-methylpyrazole-3-carboxamide--;

Column 28, claim 2, line 67 to column 29, line 1: replace: "said at least one polymer other than polydextrose" with --copovidone--;

Column 29, claim 11, lines 38-39: replace: "N-piperidino-5-(4-bromphenyl)-1-(2,4-dichlorophenyl)-4-methylpyrazole-3-carboxamide" with --N-piperidino-5-(4-bromophenyl)-1-(2,4-dichlorophenyl)-4-methylpyrazole-3-carboxamide--;

Column 29, claim 12, lines 43-45: replace: "N-piperidino-5-(4-bromphenyl)-1-(2,4-dichlorophenyl)-4-methylpyrazole-3-carboxamide" with --N-piperidino-5-(4-bromophenyl)-1-(2,4-dichlorophenyl)-4-methylpyrazole-3-carboxamide--;

Column 30, claim 17, line 15: replace: "consisting in" with --consisting of--.

Signed and Sealed this  
Ninth Day of February, 2016

Michelle K. Lee  
*Director of the United States Patent and Trademark Office*